United States Patent
Do et al.

(10) Patent No.: US 8,313,504 B2
(45) Date of Patent: Nov. 20, 2012

(54) FOAM MATRIX EMBOLIZATION DEVICE

(75) Inventors: Hiep Q. Do, Hillsborough, NJ (US);
Richard Champion Davis, III, Hollywood, FL (US); Donald K. Jones, Lauderhill, FL (US); Juan A. Lorenzo, Davie, FL (US); Vladimir Mitelberg, Aventura, FL (US); Darren R. Sherman, Ft. Lauderdale, FL (US); Murty Vyakarnam, South Orange, NJ (US)

(73) Assignee: Cordis Corporation, Miami Lakes, FL (US)

( * ) Notice: Subject to any disclaimer, the term of this patent is extended or adjusted under 35 U.S.C. 154(b) by 2148 days.

(21) Appl. No.: 11/171,560

(22) Filed: Jun. 30, 2005

(65) Prior Publication Data
US 2006/0058834 A1     Mar. 16, 2006

Related U.S. Application Data

(63) Continuation-in-part of application No. 10/775,398, filed on Feb. 10, 2004, now Pat. No. 6,979,344, which is a continuation of application No. 09/663,768, filed on Sep. 18, 2000, now Pat. No. 6,723,108.

(51) Int. Cl.
*A61M 29/00* (2006.01)
(52) U.S. Cl. ........................................... 606/200
(58) Field of Classification Search .................. 606/200; 623/1.15
See application file for complete search history.

(56) References Cited

U.S. PATENT DOCUMENTS

| | | | |
|---|---|---|---|
| 4,517,979 A | 5/1985 | Pecenka | |
| 4,544,367 A | 10/1985 | Vossen | |
| 4,550,126 A | 10/1985 | Lorenz | |
| 4,890,612 A | 1/1990 | Kensey | |
| 4,994,069 A | 2/1991 | Ritchart et al. | |
| 5,061,274 A | 10/1991 | Kensey | |
| 5,108,407 A | 4/1992 | Geremia et al. | |
| 5,122,136 A | 6/1992 | Guglielmi et al. | |
| 5,334,210 A | 8/1994 | Gianturco | |
| 5,382,259 A | 1/1995 | Phelps et al. | |
| 5,527,338 A | 6/1996 | Purdy | |
| 5,690,671 A * | 11/1997 | McGurk et al. | 606/200 |
| 5,690,761 A | 11/1997 | Masaoka | |
| 5,749,894 A | 5/1998 | Engelson | |
| 5,766,219 A | 6/1998 | Horton | |

(Continued)

FOREIGN PATENT DOCUMENTS
DE     233 303 A1     2/1986
(Continued)

OTHER PUBLICATIONS

European Search Report dated Oct. 12, 2006.
(Continued)

*Primary Examiner* — Ryan Severson (57) ABSTRACT

The present invention relates to a medical device for placement at a predetermined location within a passageway of the human body, and more particularly, relates to a flexible embolization device which may be delivered by a catheter to a pre-selected position within a blood vessel to thereby embolize a blood vessel or a blood vessel defect, such as an aneurysm or fistula. Specifically, the embolization device comprises an elongated coil having a lumen, the coil and lumen being at least partially embedded in an elongated foam member comprising, in some embodiments, a flexible, biodegradable, water insoluble, open, interconnecting-cell foam material having embolic characteristics, and capable of allowing cell proliferation into the open cell foam interior.

9 Claims, 4 Drawing Sheets

U.S. PATENT DOCUMENTS

| | | | |
|---|---|---|---|
| 5,776,184 A | 7/1998 | Tuch | |
| 5,823,198 A | 10/1998 | Jones et al. | |
| 5,833,705 A | 11/1998 | Ken et al. | |
| 5,853,418 A | 12/1998 | Ken et al. | |
| 5,891,192 A | 4/1999 | Murayama et al. | |
| 5,891,558 A | 4/1999 | Bell et al. | |
| 5,895,407 A | 4/1999 | Jayaraman | |
| 5,904,703 A | 5/1999 | Gilson | |
| 5,980,550 A * | 11/1999 | Eder et al. | 606/191 |
| 6,015,424 A | 1/2000 | Rosenbluth et al. | |
| 6,113,629 A | 9/2000 | Ken | |
| 6,159,165 A | 12/2000 | Ferrera et al. | |
| 6,165,193 A | 12/2000 | Greene, Jr. et al. | |
| 6,165,198 A | 12/2000 | McGurk et al. | |
| 6,201,065 B1 | 3/2001 | Pathak et al. | |
| 6,238,403 B1 | 5/2001 | Greene, Jr. et al. | |
| 6,245,090 B1 | 6/2001 | Gilson et al. | |
| 6,299,619 B1 | 10/2001 | Greene, Jr. et al. | |
| 6,306,424 B1 * | 10/2001 | Vyakarnam et al. | 424/426 |
| 6,355,699 B1 | 3/2002 | Vyakarnam et al. | |
| 6,375,669 B1 | 4/2002 | Rosenbluth et al. | |
| 6,723,108 B1 | 4/2004 | Jones et al. | |
| 7,112,417 B2 | 9/2006 | Vyakarnam et al. | |
| 2004/0059370 A1 | 3/2004 | Greene | |
| 2005/0137623 A1 | 6/2005 | Jones et al. | |

FOREIGN PATENT DOCUMENTS

| | | | |
|---|---|---|---|
| EP | 0547530 | | 6/1993 |
| EP | 0608139 A | | 7/1994 |
| EP | 1188414 A | | 3/2002 |
| JP | 2001-049018 | | 2/2001 |
| WO | WO 92/01433 | | 2/1992 |
| WO | WO 94/06460 | | 3/1994 |
| WO | WO 99/23954 | | 5/1999 |
| WO | WO 99/29260 | * | 6/1999 |

OTHER PUBLICATIONS

European Search Report dated Mar. 21, 2007.
European Search Report dated Sep. 26, 2006.

* cited by examiner

FOAM MATRIX EMBOLIZATION DEVICE

CROSS-REFERENCE TO RELATED APPLICATION(S)

This patent application is a continuation in part of U.S. patent application Ser. No. 10/775,398, filed Feb. 10, 2004, now U.S. Pat. No. 6,979,344 which is a continuation of U.S. patent application Ser. No. 09/663,768, filed on Sep. 18, 2000, entitled, "Foam Matrix Embolization Device", now U.S. Pat. No. 6,723,108.

BACKGROUND OF THE INVENTION

1. Field of the Invention

The present invention relates to a medical device for placement at a predetermined location within a passageway of the human body, and more particularly, relates to a flexible embolization device which may be delivered by a catheter to a pre-selected position within a blood vessel to thereby embolize a blood vessel or a defect in a blood vessel, such as an aneurysm or fistula.

Elongated coil embolization devices are well known in their use to embolize a blood vessel or a defect in a blood vessel such as an aneurysm or fistula, for example a brain aneurysm.

These embolic coils are of small diameter, on the order of 0.012 inch, for example, to have the capability of fitting into small blood vessels. Embolic coils have great advantage over neurosurgical clipping, and are quickly becoming the desired standard of care.

Embolic coils are placed into an aneurysm, which causes clotting to take place in the aneurysm, reducing the risk of aneurysm rupture. The aneurysm becomes protected by the clot, which occupies the volume of the aneurysm. However, a large number of aneurysms tend to recanalize with pressurized blood over time, which once again elevates the risk of aneurysm rupture, or growth of the aneurysm in size, along with causing compaction of the coils.

There is a need for a better, bioactive embolization device. The device of this invention is very flexible to ensure good packing. The device also enhances protein binding and cell attachment, so that the ingrowth of tissue into the aneurysm is encouraged, providing by the presence of living tissue a long-term solution to the problem of recanalization of an aneurysm.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407 to Geremia, et al., entitled "Method and Apparatus for Placement of an Embolic Coil" and U.S. Pat. No. 5,122,136 to Guglielmi, et al., entitled "Endovascular Electrolytically Detachable Guidewire Tip for the Electroformation of Thrombus in Arteries, Veins, Aneurysms, Vascular Malformations and Arteriovenous Fistulas." These patents disclose devices for delivering embolic coils at predetermined positions within vessels of the human body in order to treat aneurysms, or alternatively, to occlude the blood vessel at a particular location.

Elongated, embolic coils, which are placed in vessels, may take the form of helically wound coils, or, alternatively, may be random wound coils, coils wound within other coils or other such coil configurations. Examples of various coil configurations are disclosed in U.S. Pat. No. 5,334,210 to Gianturco, entitled, "Vascular Occlusion Assembly" and U.S. Pat. No. 5,382,259 to Phelps, et al., entitled, "Vasoocclusion Coil With Attached Tubular Woven or Braided Fibrous Coverings." Embolic coils are generally formed of radiopaque material, such as platinum, gold, tungsten or alloys of these metals. Often times several coils are placed at a given location in order to occlude the flow of blood through the vessel by promoting thrombus formation at the particular location.

In the past, embolic coils have been placed within the distal end of a catheter, and when the distal end of the catheter is properly positioned the coil may then be pushed out of the end of the catheter with, for example, a guidewire, to release the coil at the desired location. This procedure for placement of the embolic coil is conducted under fluoroscopic visualization such that the movement of the coil through the vasculature of the body may be monitored, and the coil may be placed in the desired location.

Other embolization devices, such as detachable balloons, are placed in blood vessels or aneurysms. These balloons usually take the form of an inflatable, elastic balloon with a valve assembly for sealing the balloon when a desired inflation is reached. Examples of various detachable balloons are disclosed in U.S. Pat. No. 4,517,979 to Pecenka, entitled, "Detachable Balloon Catheter" and U.S. Pat. No. 4,545,367 to Tucci, entitled "Detachable Balloon Catheter and Method of Use." Detachable balloons are generally formed of a flexible polymer and are inflated with a radiopaque solution for visualization under fluoroscopy. Often several balloons are used to fill the aneurysm space. These balloons do not generally conform to the aneurysm space, thereby leaving unoccupied space leading to an incomplete aneurysm embolization. Often times a balloon valve may leak, thereby causing other balloons to shift position, which may, in turn, occlude the parent artery, leading to severe complications.

SUMMARY OF THE INVENTION

By this invention, a vascular embolization device comprises an elongated coil having a lumen. The coil is at least partially embedded in an open interconnecting foam made from synthetic polymers or natural polymers. More specifically, the coil may be substantially fully embedded in an elongated foam member comprising a typically flexible, biodegradable, open and interconnecting cell foam material having embolic characteristics, and capable of allowing cell proliferation into the cell foam interior. The elongated, flexible foam material typically is water insoluble, and has an uncompressed outer diameter that is no more than about 0.006 inch greater than the outer diameter of the elongated coil. Preferably, this uncompressed, outer diameter of the elongated foam member is no more than about 0.004 inch greater than the elongated coil outer diameter. Some or all of the lumen of the coil may also be filled with the foam material.

Thus, by this invention, the vascular embolization device with the embedded, elongated coil remains capable of sliding through appropriate catheters for implantation into a desired position in the vascular system of a patient, while at the same time a substantial surface area of foam material having embolic characteristics is provided. As stated, the foam is capable of allowing cell proliferation into the foam interior, so that the embolization device has sufficient cell adhering surface area to be effective, while being capable of sliding through a catheter that is little or no larger than the catheter used to emplace uncoated embolization coils. Preferably, the uncompressed, outer diameter of the foam member is no more than about 0.016 inch, while the outer coil diameter, embedded therein, is about 0.01 to 0.014 inch. Typically, the uncompressed, outer diameter of the foam member is no more than 25 percent greater than the coil outer diameter, while the coil lumen is substantially filled with the foam member.

In some embodiments, the foam member comprises a polymer formulation that can be both synthetic and naturally derived, and that is flexible and cohesive, with or without the presence of water: i.e., it is not a hydrogel that must be hydrated to be desirably soft and flexible. Specifically, the foam member may be elastomeric, and may comprise a variety of different, biodegradable, water insoluble, open and interconnecting-cell foams having embolic characteristics.

Biodegradable polymers readily break down into small segments when exposed to moist body tissue. The segments then either are absorbed by the body, or passed by the body. More particularly, the biodegraded segments do not elicit permanent, chronic foreign body reaction, because they are absorbed by the body or passed from the body, such that no permanent trace or residual of the segment is retained by the body.

The biodegradable polymers that can be used according to the present invention include conventional biocompatible, biodegradable polymers including polymers selected from the group consisting of aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), poly(ester urethane), biomolecules (i.e., biopolymers such as collagen, elastin, biodegradable starches etc.) polyglycolides, polylactides, polylactones and blends thereof.

As used herein, the term "polyglycolide" is understood to include polyglycolic acid. Further, the term "polylactide" is understood to include polymers of L-lactide, D-lactide, meso-lactide, blends thereof, and lactic acid polymers and copolymers in which other moieties are present in amounts less than 50 mole percent.

Currently, aliphatic polyesters are among the biodegradable polymers for use in making the foam portion of the foam implants according to the present invention. Aliphatic polyesters can be homopolymers, copolymers (random, block, segmented, tapered blocks, graft, triblock, etc.) having a linear, branched, or star structure. Suitable monomers for making aliphatic homopolymers and copolymers may be selected from the group consisting of, but are not limited to, lactic acid (both L- and D-isomers), lactide (including L-, D-, and meso-lactide), glycolic acid, glycolide, epsilon-caprolactone, p-dioxanone (1,4-dioxan-2-one), trimethylene carbonate (1,3-dioxan-2-one), and combinations thereof.

Elastomeric copolymers are also particularly useful in the present invention. Suitable elastomeric polymers include those with an inherent viscosity of 0.8 dL/gram or greater, in some embodiments about 1.2 dL/gram to 4 dL/gram, and in other embodiments about 1.4 dL/gram to 2 dL/gram, as determined at 25° C. in a 0.1 gram per deciliter (gram/dL) solution of polymer in hexafluoroisopropanol (HFIP). Further, suitable elastomers exhibit a high percent elongation and a low modulus, while possessing good tensile strength and good recovery characteristics. In one embodiment of this invention, the elastomer from which the foam component is formed exhibits a percent elongation (e.g., greater than about 200 percent and sometimes greater than about 500 percent). In addition to these elongation and modulus properties, suitable elastomers should also have a tensile strength greater than about 500 psi, sometimes greater than about 1,000 psi, and a tear strength of greater than about 50 lbs/inch, or even greater than about 80 lbs/inch.

Exemplary biodegradable, biocompatible elastomers include but are not limited to elastomeric copolymers of epsilon-caprolactone and glycolide (including polyglycolic acid) with a mole ratio of epsilon-caprolactone to glycolide of from about 35/65 to about 65/35, or from 45/55 to 35/65; elastomeric copolymers of epsilon-caprolactone and lactide (including L-lactide, D-lactide, blends thereof, and lactic acid polymers and copolymers) where the mole ratio of epsilon-caprolactone to lactide is from about 30/70 to about 95/5 and in some embodiments from 30/70 to 45/55 or from about 85/15 to about 95/5; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40/60 to about 60/40; elastomeric copolymers of epsilon-caprolactone and p-dioxanone where the mole ratio of epsilon-caprolactone to p-dioxanone is from about from 30/70 to about 70/30; elastomeric copolymers of p-dioxanone and trimethylene carbonate where the mole ratio of p-dioxanone to trimethylene carbonate is from about 30/70 to about 70/30; elastomeric copolymers of trimethylene carbonate and glycolide (including polyglycolic acid) where the mole ratio of trimethylene carbonate to glycolide is from about 30/70 to about 70/30; elastomeric copolymers of trimethylene carbonate and lactide (including L-lactide, D-lactide, blends thereof, and lactic acid polymers and copolymers) where the mole ratio of trimethylene carbonate to lactide is from about 30/70 to about 70/30); and blends thereof. It is to be understood that the exemplary biodegradable, biocompatible elastomers may be generally synthesized by a ring-opening polymerization of the corresponding lactone monomers or by polycondensation of the corresponding hydroxyacids, or by combinations of these two polymerization methodologies.

One of ordinary skill in the art will appreciate that the selection of a suitable polymer or copolymer for forming the foam depends on several factors. The more relevant factors in the selection of the appropriate polymer(s) that is used to form the foam component include biodegradation kinetics; in-vivo mechanical performance; cell response to the material in terms of cell attachment, proliferation, migration and differentiation; and biocompatibility. Other relevant factors, which to some extent dictate the in-vitro and in-vivo behavior of the polymer, include the chemical composition, spatial distribution of the constituents, the molecular weight of the polymer, and the degree of crystallinity.

The ability of the material substrate to biodegrade in a timely fashion in the body environment is also significant. But the differences in the biodegradation time under in vivo conditions can also be the basis for combining two different copolymers. For example, a copolymer of 35/65 epsilon-caprolactone and glycolide (a relatively fast biodegrading polymer) is blended with 40/60 epsilon-caprolactone and L-lactide copolymer (a relatively slow biodegrading polymer) to form a foam component. Depending upon the processing technique used, the two constituents can be either randomly interconnected, bicontinuous phases, or the constituents could have a gradient-like architecture in the form of a laminate type composite with a well integrated interface between the two constituent layers. The microstructure of these foams can be optimized for the required application.

In one embodiment it is desirable to use polymer blends to form structures which transition from one composition to another composition in a gradient-like architecture. For example, by blending an elastomer of epsilon-caprolactone-co-glycolide with epsilon-caprolactone-co-lactide (e.g., with a mole ratio of about 5/95) a foam may be formed that transitions from a softer, spongy material to a stiffer, more rigid material. Clearly, one of ordinary skill in the art will appreciate that other polymer blends may be used for similar gradient effects, or to provide different gradients (e.g., different biodegradation profiles, stress response profiles, or different degrees of elasticity).

Methods for manufacturing the foam component of the current device include a variety of methods known and used in this art. For example, they include lyophilization, supercritical solvent foaming, extrusion or mold foaming with fugitives (e.g. external gas injection or in situ gas generation), casting with an extractable material (e.g., salts, sugar or similar suitable materials) and the like.

Of particular utility is foam formation by freeze drying or lyophilization. The advantages of lyophilization include the avoidance of elevated temperatures, thus minimizing the potential for temperature-associated degradation and enabling the inclusion of temperature sensitive bioactive agents. Additional advantages include the ability to control the pore size and porosity of the foamed material. Non-aqueous lyophilization also eliminates the need for exposure of the processed material to water, as is required in salt leaching processes that may cause premature hydrolysis. Lyophylization is a cost effective, simple, one-step process that facilitates manufacturing, and is widely known and used in the food and pharmaceutical industries.

Lyophilization is a process for removing a (frozen or crystallized) solvent, frequently water, from various materials. Lyophilization of enzymes, antibodies, and sensitive biological materials is quite often the method of choice for extending the shelf life of these products and preserving their biological activity. As practiced as a means of foam formation, the lyophilization process usually requires that a polymeric material be rendered soluble in a crystallizable solvent capable of being sublimed, usually at reduced pressure. Although the solvent may be water, other solvents such as 1,4-dioxane are commonly used. This latter solvent has found great utility in foam formation because many medically important polymers are soluble in it. It is crystallizable (melting point approximately 12° C.), and it can generate a significant vapor pressure at temperatures in which it is still a solid, i.e. it can be sublimed at reduced pressure.

While portions only of the entire length of the elongated coil may be embedded in separate lengths of the elongated foam member, in other embodiments, the entire length of the elongated coil is embedded in the elongated foam member.

The elongated coil may be made of conventional materials for use as a vascular embolization device, for example, platinum, gold, tungsten, titanium, or suitable alloys thereof.

In some embodiments, the elongated foam member has an average pore size of 5-500 microns, which permits the desired cell proliferation into the open cell foam interior.

The porous foam member in which the elongated coil is embedded is desirably elastomeric (i.e. having an elongation to break of at least 100%) to permit compression of the body within a catheter, although by this invention only a relatively minor amount of the mass of the elongated foam member is outside of the coil and, thus, needing compression when placed in the catheter.

Also, a flexible, elastomeric material is less likely to chip off, thus avoiding fragments that can form emboli elsewhere in the body, which is of course highly undesirable.

By this means, an easily deployable, vascular embolization device is provided which has less tendency to encounter the subsequent problem of recanalization, since the porous foam increases protein binding and cell attachment to encourage tissue ingrowth, which is a long-term solution to the recanalization problem. By this invention, tissue response can be modulated in such a way that, rather than triggering a severe thrombolitic response, protein binding and cell attachment is enhanced. A mild to moderate inflammatory response can be induced that promotes organization of fibrotic tissue, leading to the desired tissue ingrowth. Also, the packing density of the embolization devices of this invention can be higher than uncoated coils of the prior art, since the porous layer expands as it exits from the catheter, forming its natural, unstressed size, with a diameter which is slightly larger than the coils embedded in them. Thus, more of the aneurysm is filled, resulting in more blood stagnation for forming the initial clot, and compensating for the natural contours of an aneurysm shape, to provide better outcomes.

Preferably, the coating composition of this invention comprises a known, elastomeric, foamed copolymer of epsilon caprolactone and glycolide (referred to hereafter as PCL/PGA). Unlike collagen-based coatings, the PCL/PGA coating is not pro-thrombolitic, thereby allowing the surgeon to manipulate the precise location of the embolization device for deployment. Furthermore, the PCL/PGA coating can provide consistent deployment, not significantly altering the physical characteristics of the coil. The degree of pro-inflammatory response can be controlled by changing the amount and formulation of the polymer coated on the coil, changing the nature of the composition, or adding of low molecular weight glycolide or glycolic acid monomers.

The elongated coils used herein are known to the art and are generally metallic, being introduced into a neurovascular space, for example, using an image guided system. The coils are preformed during manufacturing to attain random or helical shapes that easily conform to a space such as an aneurysm. Once deployed at the proper location within the vascular system of the patient, they are detached from the delivery system, such as a catheter, by conventional means. The coils generally retain their pre-formed shapes, to ensure integrity of the filling of the aneurysm or the like, and to reduce the chance of migration of the coil from the aneurysm sac into the vasculature.

The foamed, porous polymers may be created by known physical or chemical means. However, a preferred method of making a porous, vascular embolization device with an embedded, elongated coil comprises the steps of: creating a generally homogeneous solution (which includes dispersions such as colloids) of the desired polymer from which the foam member is made; placing the coil in a tubular mold and filling the mold with the polymer solution; cooling the mold at a desired cooling rate for the polymer solution to separate into phases; and lyophilizing (vacuum drying) the polymer solution, to remove the solvent essentially by sublimation or evaporation, thus forming the elongated foam member with the coil embedded therein.

A drying step or an annealing step may also be used if desired, to provide a solvent-free, stable, porous, elongated foam member with the coil embedded therein, and which has a long shelf life. Porosity (pore density), pore size, and surface area of the elongated foam member can be controlled by process variables such as polymer solution concentration, the particular polymer-solvent system used, the cooling rate, and a ratio of the coil outer diameter to the inner diameter of the tube in which the coil resides during the process.

Other methods of creating porous coils can include the introduction of a fugitive compound, such as a soluble salt, that is not actually a solvent, but can be admixed into the polymer solution or polymer melt, and, once the device is coated or filled into a mold and subsequently dried or cooled, the fugitive compound can be removed by dissolution in a suitable solvent, such as water. Such materials are deemed to be a "solvent" herein for the purpose of defining the invention.

Alternatively, the fugitive compound can be a blowing agent for creation of the foam by forming bubbles.

Furthermore, the porous polymer of the elongated foam member can act as a depot for controlled release of a therapeutic agent. For example, a chemotactic agent can be present to induce cellular activity.

In another aspect of the invention, a method is provided for making a coated, vascular embolization device, which comprises: inserting an uncoated, vascular embolization coil into an inert, typically plastic tubing (which acts as a mold); filing the tubing with a generally homogeneous solution of a coating material for the coil; freezing the solution to form a multiple-phase, frozen mass in the tubing; and lyophilizing the frozen mass in the tubing to remove solvent therefrom, forming a porous coating on said coil. The coating formed may be an open cell foam coating, in currently preferred embodiments, for the advantages stated above.

In some embodiments, the inner plastic tubing may have an inner diameter of about 0.013 to 0.03 inch. The vascular embolization coil may have a diameter of about 0.01 to 0.02 inch.

The coating material may, in currently preferred embodiments, consist essentially of a PCL/PGA copolymer.

The solution contained in the tube may, in the step of freezing or cooling, be frozen in ice water, a mixture of dry ice and methanol, liquid nitrogen, or another cryogenic fluid.

As above, the elongated coil may be made of the normal materials used for an embolic coil, such as platinum and others listed above.

Furthermore, in accordance with one aspect of the present invention, the vascular embolization system comprises a catheter, a push rod and an embolization device. The embolization device takes the form of an embolization coil surrounded by a foam sleeve. The foam sleeve has a hydrated, normal, expanded diameter. However it may be compressed and remain compressed when constrained. When the foam sleeve is hydrated and unconstrained, the foam sleeve will return to its normal, expanded diameter. The embolization device is positioned in the lumen of the catheter. The push road is slidably received by the lumen of the catheter and engages the embolization device. Distal movement of push rod causes the embolization device to exit the lumen of the catheter at a predetermined site within a blood vessel.

In some embodiments, a vascular embolization system is provided for treating a defect in a blood vessel comprising: a catheter having a proximal section, a distal section, and an outer wall defining a lumen therethrough; a push rod slidably disposed within the lumen of said catheter having a proximal end and distal end; and an embolization device comprising an elongated, helical coil formed into a secondary helical configuration and cylindrical foam sleeve disposed about said coil, said cylindrical foam sleeve having a hydrated, normal expanded diameter and a smaller, constrained diameter such that when unconstrained and hydrated, said cylindrical foam sleeve returns to the normal, expanded diameter. The embolization device may be disposed within the lumen at the distal section of the catheter. The distal end of the push rod engages the embolization device such that distal movement of the push rod causes the embolization device to exit the lumen of the catheter at a pre-selected position within the blood vessel.

The embolization device may comprise a radiopaque material and/or a therapeutic agent. Also, the cylindrical foam sleeve may have a larger normal, expanded diameter than the diameter of the lumen of the catheter or, alternatively, a smaller normal, expanded diameter than the outer diameter of the catheter.

The cylindrical foam sleeve may be a moldable foam material that is bonded to the coil. The cylindrical foam sleeve may also comprise a hydrogel, in some embodiments. The embolization device may also include a reinforcing material, such as at least one fiber.

The embolization device may take a convoluted shape in its normal, unstressed configuration.

In accordance with another aspect of the present invention, there is provided an embolization system comprising an embolization device, which takes the form of an embolization coil, which is impregnated and surrounded by a foam sleeve made of a moldable material. Preferably, the foam sleeve extends into the lumen of the coil.

In another aspect of the present invention there is provided an embolization system, which includes an embolization device having an embolization coil and a foam sleeve bonded to the coil. The embolization device takes the form of a helix. The embolization device is positioned in the lumen of a catheter in a generally straightened configuration, however, upon exiting the distal lumen of the catheter the embolization device returns to the relaxed helical shape. Alternately, the embolization device may take the form of a convoluted shape.

In accordance with another aspect of the present invention there is provided an embolization device that comprises an embolization coil with a foam sleeve disposed about the periphery of the coil. The foam may take the form of a hydrogel and in addition, the embolization device may be used to deliver a therapeutic agent to improve the efficiency of a particular treatment modality. The choice of therapeutic agent depends largely on the particular treatment chosen for a vascular abnormality. In the treatment of an aneurysm the therapeutic agent may be a growth factor such as fibroblast growth factor (FGF) or vascular endothelial growth factor (VEGF) to promote endothelialization and permanent occlusion of the aneurysm. Other therapeutic agents include radioactive materials to aid in the treatment of arteriovenous malformations. Other therapeutic agents include drugs used to obliterate tumors.

In accordance with yet another aspect of the present invention, there is provided an embolization device having an embolization coil and foam sleeve disposed about the coil periphery, which is radiopaque. The embolization device may be made visible under fluoroscopy by using an embolization coil made from a radiopaque material such as a platinum or tungsten alloy. Alternatively, the foam sleeve may be made radiopaque by incorporating a radiopaque filler material such tantalum or tungsten powder or a radiopaque iodine commonly used in contrast media such as RENOGRAFFIN. This radiopaque material aids in the visualization of the embolization device during the medical procedure.

In still another aspect of the present invention there is provided an embolization device that comprises an embolization coil and a foam sleeve bonded to the coil. The embolization coil may contain reinforcing fiber or fibers that are secured in at least two locations and extend through the lumen of the coil to reduce coil stretching. Alternatively, the foam sleeve may contain reinforcing material dispersed throughout the foam, such as long fibers to resist stretching or short fibers or particles to improve sponge mechanical integrity.

In accordance with another aspect of the present invention there is provided an embolization device that comprises an embolization coil surrounded by a foam sleeve. The foam sleeve has a hydrated normal, expanded diameter, however, it can be compressed and remain compressed when constrained. When the foam sleeve is hydrated and unconstrained the foam sleeve will return to its normal expanded diameter. Typically the normal expanded diameter of the foam sleeve is larger than the diameter of the lumen of the catheter.

In accordance with another aspect of the present invention there is provided an embolization device that comprises an embolization coil surrounded by an open-celled elastomeric foam covering. The foam covering has a normal diameter, which is typically smaller than the lumen of the catheter. The foam covering may also extend to the interior lumen of the embolization coil.

In accordance with still another aspect of the present invention there is provided an embolization device that comprises an embolization coil surrounded by a foam-like polymer network having elastic properties. The foam-like polymer network has an open porous structure and a normal diameter that is typically smaller than the lumen of the catheter. The foam-like polymer network may also extend to the interior lumen of the embolization coil.

In accordance with yet another aspect of the present invention there is provided an embolization device that comprises an embolization coil surrounded by a foam sleeve. The foam sleeve has a hydrated normal, expanded diameter, however, it can be compressed and remain compressed when constrained. When the foam sleeve is hydrated and unconstrained the foam sleeve will return to its normal, expanded diameter. Typically, the normal, expanded diameter of the foam sleeve is smaller than the diameter of the catheter used to deliver the embolization device.

In accordance with another aspect of the present invention there is provided a vascular embolization system comprising a push rod, a catheter and an embolization device. The embolization device takes the form of an elongated, flexible, cylindrical, resilient foam. The foam has a normal hydrated, expanded diameter and a smaller constrained diameter. When the foam is unconstrained and hydrated, the foam returns to the normal, expanded diameter. This elongated flexible foam has a length that is at least ten times greater than the normal, hydrated diameter.

In another aspect of the present invention there is provide an embolization device, which takes the form of an elongated flexible foam. The foam may take the form of a hydrogel. The foam may be used to deliver therapeutic agents to improve the efficacy of a particular treatment modality.

In yet another aspect of the present invention there is provided an embolization device, which takes the form of an elongated flexible cylindrical foam. To improve then mechanical integrity of the foam, the foam may contain reinforcing materials. Reinforcing materials may take the form of long fiber or fibers incorporated within the foam or short fibers or particles dispersed throughout the foam.

In still another aspect of the present invention there is provided an embolization device, which takes the form of an elongated, flexible foam. The foam may be made visible under fluoroscopy by incorporating a radiopaque filler material such tantalum or tungsten powder or a radiopaque iodine commonly used in contrast media such as RENOGRAFFIN. This radiopaque material aids in the visualization of the embolization device during the medical procedure.

In accordance with yet another aspect of the present invention there is provided an embolization system comprising a push rod, a catheter, and an embolization device. The embolization device takes the form of an elongated, resilient flexible foam having an elongated length that is at least ten times the normal expanded diameter. The foam takes the shape of a helix. The embolization device is positioned in the lumen of the catheter in a generally straightened configuration. The push rod is slidably disposed into the catheter lumen engaging the embolization device. Distal movement of the push rod causes the embolization device to exit the lumen of the catheter. As the embolization device exits the distal section of the catheter lumen and enters the blood vessel, the embolization device returns to its relaxed, helical shape. Alternately, in treating a blood vessel defect such as an aneurysm, the embolization may have a preferred, convoluted shape.

In accordance with another aspect of the present invention there is provided an embolization system comprising a push rod, a catheter and an embolization device. The embolization device takes the form of an elongated, flexible, resilient, cylindrical foam. The foam has a normal, expanded diameter when hydrated and a smaller compress diameter when constrained. The normal, expanded diameter of the foam may be larger than the diameter of the lumen of the catheter.

In accordance with another aspect of the present invention there is provided an embolization system comprising a push rod, a catheter and an embolization device. The embolization device takes the form of an elongated, flexible, resilient, cylindrical foam. The foam has a normal, expanded diameter when hydrated and a smaller compressed diameter when constrained. The normal, expanded diameter of the foam material may be smaller than the diameter of the catheter used to deliver the embolization device.

In accordance with yet another aspect of the present invention there is provided a vascular embolization system comprising a push rod, a catheter and an embolization device. The embolization device includes a flexible wire and a resilient foam sleeve disposed about the wire. The foam sleeve has a normal, hydrated, expanded diameter and a smaller, constrained diameter, such that when unconstrained and hydrated, said foam sleeve returns to the normal, expanded diameter.

DESCRIPTION OF SPECIFIC EMBODIMENTS

Figure 1:
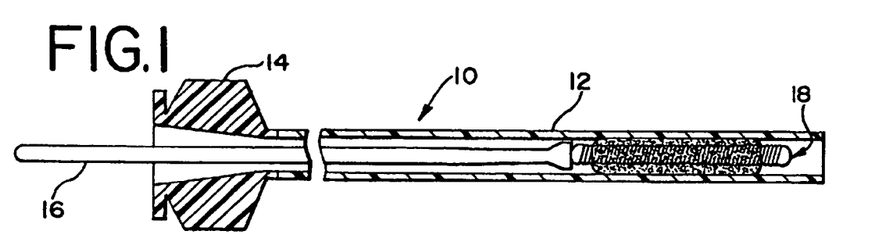
FIG. 1 illustrates a partial section view of a first embodiment of the vascular embolization system of the present invention.

FIG. 1 illustrates a first embodiment of the vascular embolization system 10. The vascular embolization system 10 includes a catheter 12, having a proximal hub 14, push rod 16 and embolization device 18. Embolization device 18 is disposed within the lumen at the distal section of catheter 12.

Push rod 16 is slidably disposed within the lumen of catheter 12, proximal to embolization device 18.

Figure 2A:
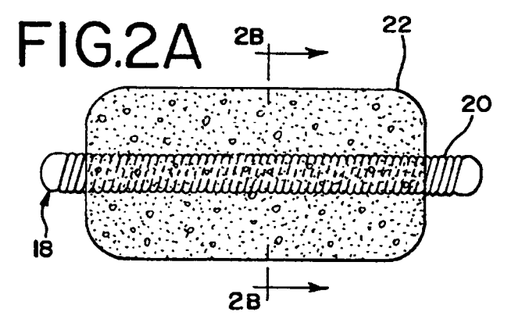
FIG. 2A illustrates an axial view of an embolization device according to the present invention.
Figure 2B:
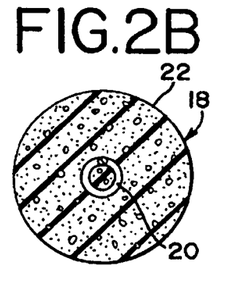
FIG. 2B illustrates a cross sectional view of the embolization device depicted in FIG. 2A.

FIGS. 2A and 2B show axial and cross sectional view of embolization device 18. The embolization device 18 comprises an embolization coil 20 surrounded by a foam sleeve 22. The embolization coil 20 is of the type commonly used to reduce or embolize a particular blood vessel. Depending on the flexibility needed and catheter system utilized, the embolization coil 20 ranges in diameter from about 0.002 inches to 0.150 inches with a preferred range of about 0.006 inches to 0.052 inches. Materials used to make the embolization coil 20 include polymers, metals or composites in filament form. A wide variety of polymers are suitable for the embolization coil such as nylons, polyesters, collagen, polyvinylalcohol, or hydrogels of polyvinylalcohol or polyvinylpyrrolidone. Metals are often used to form embolization coils that are biocompatible and provide the desired flexibility like platinum, gold and nickel-titanium alloys. The preferred materials are metals formed of platinum alloys. The foam sleeve 22 is a foam material that is secured using thermal, adhesive, or mechanical means to the embolization coil 20. As shown in FIG. 2B, embolization device 18 is illustrated in cross-section. The foam sleeve 22 is formed of a biocompatible material. Foams for use in the preferred embodiment and alternate embodiments are generally polymeric in nature and can be formed of many materials such as collagen, polyvinylalcohol (PVA), polyvinylpyrrolidone (PVP), polyurethane or polyetherpolycarbonate. In the preferred embodiment, foam sleeve 22 is molded about coil 20 using liquid components that when processed by lyophilization, form a solid, flexible foam, such as those described in U.S. Pat. No. 4,550,126. Preferably the foam material extends within the lumen of coil 20. To improve the integrity and mechanical properties of these foams, reinforcing materials can be incorporated into the foam. Typically, reinforcing material is in the form of high strength, flexible fibers; however particles are also acceptable. These foams generally have a hydrated, normal, expanded diameter and a smaller, compressed diameter when constrained. These foams are flexible and resilient, such that when unconstrained and sufficiently hydrated they return to the normal, expanded diameter. The diameter of any of the foams of the preferred embodiment are largely dependent on the catheter used and the vasculature to be occluded, but generally is in the range of about 0.01 mm to 20 mm, preferably in the range of about 0.1 mm to 5 mm. The structure of the foams, such as in foam sleeve 22 can be that of open celled, closed celled, or a combination of both; however, preferably open celled. To improve the visibility of the foams under fluoroscopy, radiopaque materials such as platinum, tungsten, tantalum, gold, barium or iodine can be incorporated within or bonded to the foam. As can be appreciated, these foams can be comprised of biocompatible hydrogel materials, such as PVA, PVP, collagen, etc., making them suitable for delivery of therapeutic agents. These therapeutic agents can include radioactive particles to deliver therapeutic radiation, growth factors such as VEGF or FGF, chemotherapy agents as well as other drugs to treat tumors.

Figure 3:
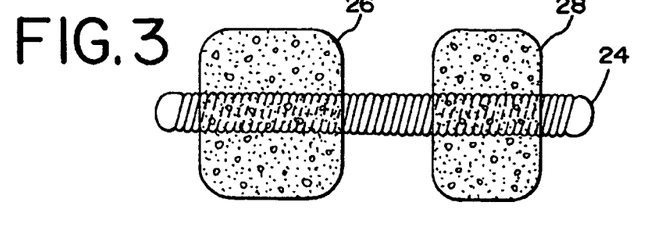
FIG. 3 illustrates an alternative embodiment of an embolization device according to the present invention.
Figures 4, 5:
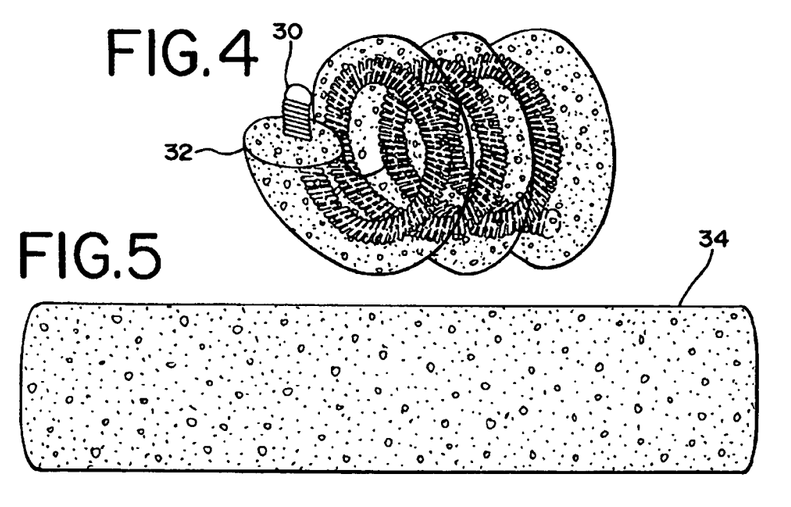
FIG. 4 illustrates another alternative embodiment of an embolization device having a helical shape according to the present invention.
FIG. 5 illustrates yet another alternative embodiment of an elongated embolization device according to the present invention.

FIGS. 3 and 4 illustrate alternate embodiments of the present invention. In a first alternate embodiment depicted in FIG. 3, foam sleeve elements 26 and 28 are disposed about coil 24. The foam sleeve elements 26 and 28 are formed onto the coil 24 using aforementioned materials and methods. As can be appreciated, only their length and the length of the coil limit the number of foam sleeve elements. The foam sleeve elements 26 and 28 generally have a cylindrical shape. A variation of the first alternate embodiment includes foam sleeve elements disposed about the coil, in which the length of one foam sleeve elements extends far distal from the end of the coil. The length the foam element that extends from the end of the coil is in the range of 10 to 500 times the length of the coil with a preferred range of about 20 to 300 times the coil length.

In a second alternate embodiment shown in FIG. 4, foam sleeve 32 is disposed about coil 30. Coil 30 is formed into a helical shape and consequently foam sleeve 32 also takes this helical shape. Alternatively coil 30 could be of a straight configuration, placed in a helical mold and foam sleeve 32 molded about coil 30 in a helical shape. As can be appreciated, the coil 30 can be shaped complex, convoluted, spherical, conical, spiral or any other shape that is suitable for occluding the blood vessel or vascular malformation.

FIG. 5 illustrates a third alternate embodiment in which the embolization device of the vascular embolization system is an elongated foam material 34. The elongated foam material 34 of the present invention is open celled, however variations could include closed cells or a combination of both. The elongated foam material 34 generally has a primary long, cylindrical shape. As can be appreciated, this long cylindrical shape can have a secondary shape that is helical, conical, spherical, complex or convoluted pertinent shape to aid in delivery or occlusion. The length of the elongated foam material 34 is at least ten times its primary diameter but preferably greater than fifteen times the primary diameter.

Figure 6A:
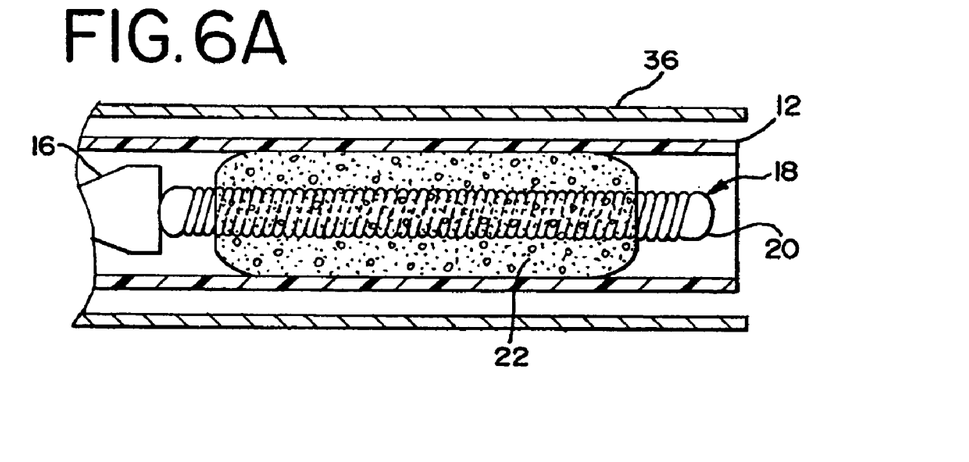
FIGS. 6A, 6B, 6C and 6D illustrate a sequence of delivery and deployment of embolization devices in a vessel according to the present invention.
Figure 6B:
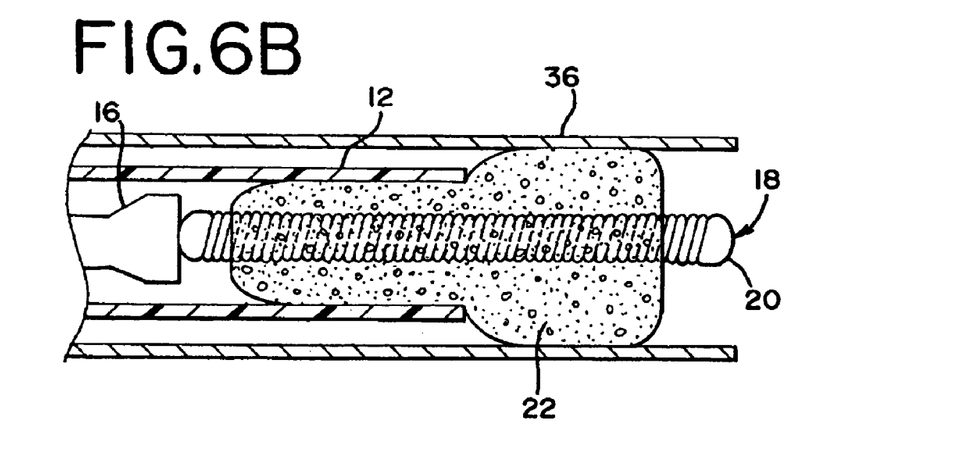
Figure 6C:
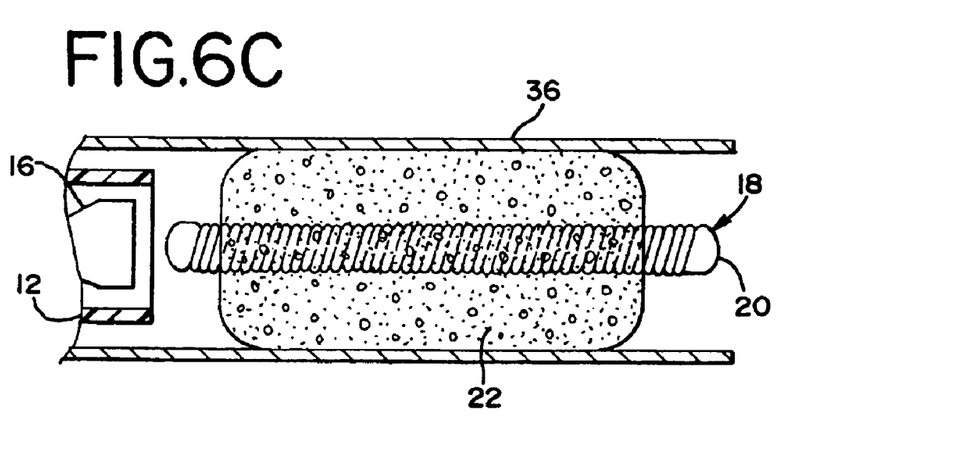
Figure 6D:
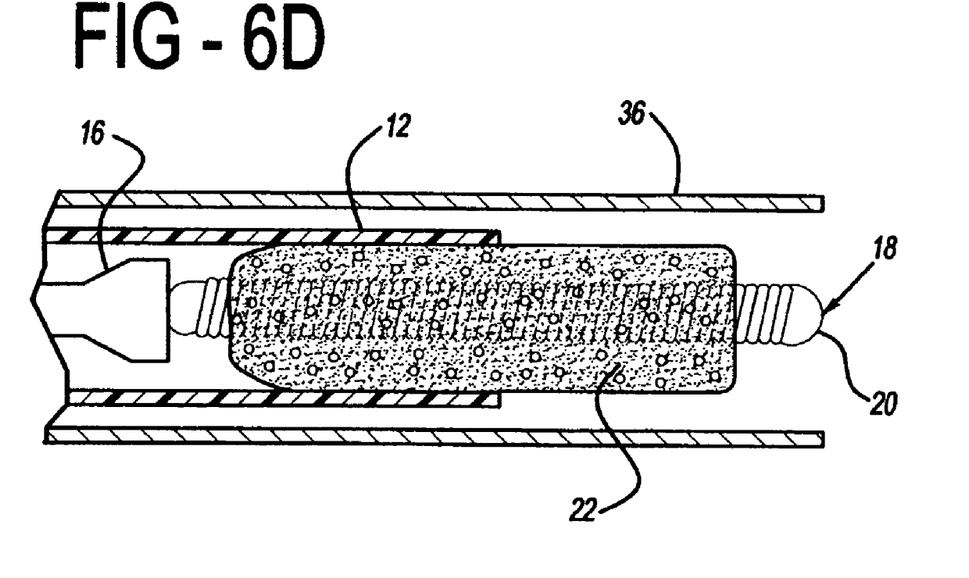

FIGS. 6A, 6B and 6C illustrate the sequence of positioning and deploying the vascular embolization system 10 within a blood vessel. FIG. 6A depicts catheter 12 properly positioned within a blood vessel 36 selected for embolization. Push rod 16 and embolization device 18 are introduced into the lumen of catheter 12. Distal movement of push rod 16 advances embolization device 18 to the distal section of catheter 12. Further distal movement of push rod 16 causes embolization device 18 to exit the lumen of catheter 12. As shown in FIGS. 6B and 6C, the embolization device 18 exits the lumen of catheter 12 and the foam sleeve 22 expands. The foam sleeve 22 expands to its hydrated, normal, expanded diameter within the vessel and thereby embolizes the vessel. In an alternate embodiment of the present invention as shown in FIG. 6D, the foam sleeve 22 of the embolization device 18 has a normal expanded diameter which is smaller than the lumen of catheter 12, such that when the embolization device 18 exits the lumen of catheter 12, the foam sleeve 22 is already at its expanded diameter.

Figure 7:
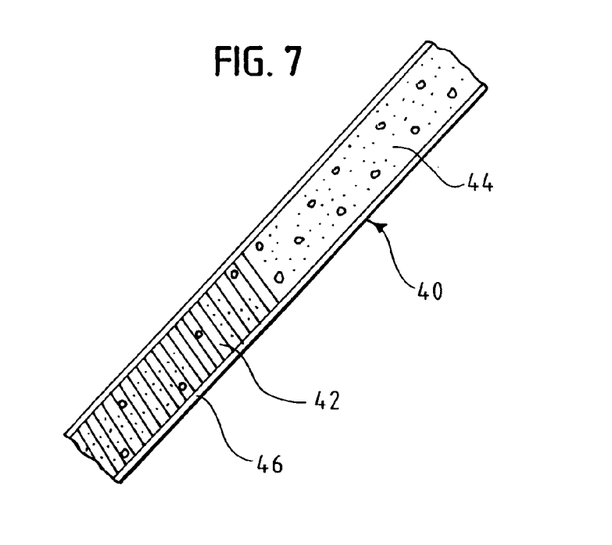
FIG. 7 is a fragmentary, enlarged view of an embolic coil in accordance with this invention, with portions broken away.

FIG. 7 shows a vascular embolization device 40, which comprises a helical embolic coil 42, which may be made of platinum or the like, and may be of conventional dimensions for an embolic coil, for example, an outer diameter of 0.012 inch. Such an embolic coil can be used in the treatment of brain aneurysms.

Only a portion of embolic coil 42 is shown. A typical embolic coil may be on the order of 10 cm. in length, and may naturally bunch up into a clump of material, to facilitate its retention in an aneurysm sack or the like. While the vascular embolization devices shown in the drawings are straight, in fact, they tend to naturally assume a nonstraight configuration, of a form as desired for the particular treatment.

Elongated coil 42 is shown to be embedded in an elongated foam member 44, which occupies the lumen of coil 42, and also typically extends outwardly between the coils of coil 42 to form a relatively thin, outer coating 46 of the same foam material as is found in the inner foam portion 44 that is occupying the lumen of coil 42. In this embodiment, the thickness of outer foam layer 46 extends about 0.001 inch beyond coil 42 surrounding coil 42 on all sides, and connected with the internal foam body 44. Thus, such an embolization device is capable of sliding in a catheter, compressing the generally cylindrical foam layer 46, without creating an undue amount of friction in a catheter, which catheter is only slightly enlarged in its inner diameter, or not enlarged at all, over a catheter that is used for the emplacement of a bare embolic coil similar to coil 42. A portion of coil 42 has been omitted in FIG. 7, to better illustrate the inner foam body 44 present in the lumen of coil 42, but, in reality, coil 42 extends the entire length of FIG. 7.

Foam body 44, 46 may be an open cell, porous foam made of a copolymer of about 36 weight percent PCL and 64 weight percent PGA, which is a known material for coating of embolic coils. Other proportions of PCL to PGA may also be used.

The open cell pores of the material used may have an average pore size of 5 to 500 microns, providing an embolization device into which cells of the body can migrate, and proliferate through the network of open cell pores of the foam into the interior thereof. The solid foam material forms a bed to receive and carry the proliferating cells. Furthermore, the foam is biodegradable, permitting the slow replacement of the foam material by proliferating tissue, the result of this being that, over time, tissue proliferates throughout the aneurysm sac, resulting in a more stable securance of the aneurysm, with reduced possibility of recanalization and the return of a dangerous condition with respect to the aneurysm.

When compared with a bare metal embolization coil, embolization devices similar to that of FIG. 1 can exhibit a significant increase in fibroblast cell adhesion over a two hour period, on the order of 33% greater. Also, there can be increase of fibronectin binding on the embolization device similar to that of FIG. 1, showing a three fold increase or more over a corresponding, bare metal embolization coil.

These improvements result in better cell proliferation through the vascular embolization devices of this invention, when compared with corresponding bare metal embolic coils.

Figure 8:
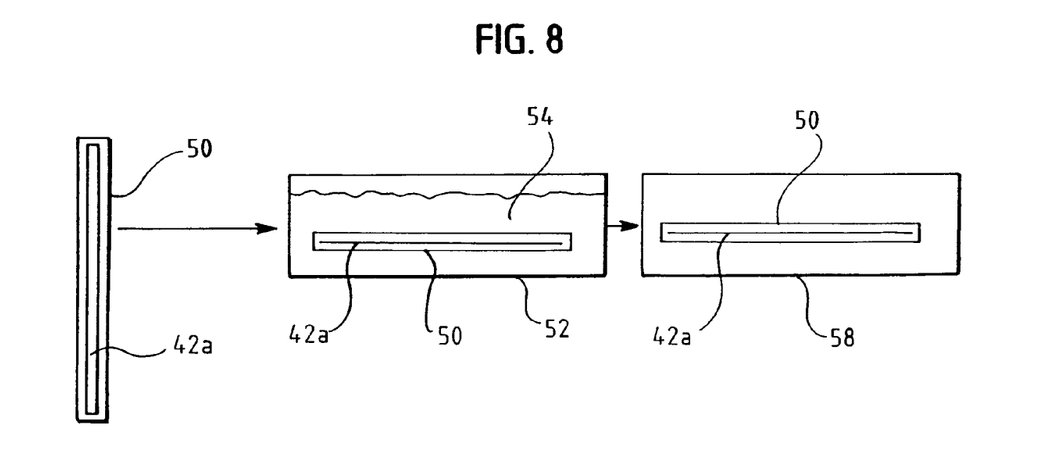
FIG. 8 is a diagrammatic view of a process for steps of manufacturing the vascular embolic coil of FIG. 7.

Turning to FIG. 8, a graphic flow chart is shown of steps used in a method for manufacturing embolization devices in accordance with this invention. A 10 cm length of a platinum embolic coil 42a is inserted into 12 cm of polytetrafluoroethylene (PTFE) tubing 50, having an inner diameter of 0.022 inch. While FIG. 8 shows the embolic coil 42a to be straight, in fact it typically has many curves and kinks, naturally folding up into a little bundle or wad, and thus would not be precisely straight as retained in tube 50. In one embodiment, the resulting tube 50 containing coil 12a is filled with a solution of 5% (w/w) of 36% PCL/64% PGA copolymer, dissolved in 1,4-dioxane from Fisher Scientific Company. When the lumen of tube 50 is completely filled, the tube is immersed into a container 52 containing liquid nitrogen 54 for five minutes. Upon the freezing of the solution with liquid nitrogen, there is a phase separation between the PCL/PGA copolymer and the 1,4-dioxane. Then, the tubing 50 and frozen solution is placed into an aluminum mold or open metal rack, dish, or plate 58, which has been pre-cooled to −17° C. The aluminum mold or rack is stored in a lyophilization (freeze-drying) chamber, under vacuum, so that the 1,4-dioxane evaporates out of the lumen of tubing 50, leaving the PCL/PGA polymer as a porous foam, carried inside and outside of embolic coil 42a. The resulting mass of PCL/PCA in which coil 42a is embedded comprises an open-cell foam.

The above disclosure, and the examples below, are for illustrative purposes only, and are not to limit the scope of the invention, which is as described in the claims below.

Example 1

Polymer Solution Preparation

A 1% w/w solution of epsilon-caprolactone/glycolide copolymer in 1,4-dioxane was prepared as follows. 1.5 grams of 36/64 poly(epsilon-caprolactone-glycolic acid) copolymer, obtained from American Polymer Incorporated (American Polymer Inc., Birmingham, Ala.), were added to 148.8 grams of 1,4-dioxane (Fisher Scientific, Raritan, N.J.) in a 250 milliliter Erlenmeyer screwed cap flask. The mixture was stirred for 4 hours in 60° C. water bath set on a temperature controlled heating plate. The polymer solution was filtered through an extra coarse thimble filter to remove any undissolved solids.

Example 2

Making 36/64 PCL/PGA Foamed Coils Using Freeze-Dry Method

A 10-cm embolic coil was inserted in a polytetrafluoroethylene (PTFE) tubing (0.015" ID, ZEUS Industrial products, Inc. Orangeburg, S.C.) that was 2 centimeters longer that the coil. The tube served as a mold. The tube mold containing the coil was filled with the 1% w/w solution of the epsilon-polycaprolactone/glycolide (PCL/PGA) copolymer in 1,4-dioxane described in Example 1, using a glass syringe with a 30 G needle attached. The tube mold containing the coil and solution was sonicated for approximately 5 minutes in a sonication bath (BRANSON, Model 3210R-DTH, Danbury, Conn.) to ensure the solution got into the inter-diameter of the coil, between the coils and into the coil lumen. Bubbles generated during sonication were replaced with fresh polymer solution. Then, the tube mold was frozen in liquid nitrogen for about five minutes, and placed on a pre-cooled (−17° C.) shelf of a freeze-dryer (lyophilization unit) (FTS Systems, Model TD3B2T5100, Stone Ridge, N.Y.) The following freeze-drying cycle was the used:

| Temp(° C.) | Pressure (mtor) | Hold time (min) |
|---|---|---|
| −17 | Ambient pressure | 15 |
| −17 | 100 | 120 |
| −5 | 20 | 120 |
| +5 | 20 | 60 |
| 20 | 20 | 60 |

Example 3

Fibronectin Absorption Experiment

A 4-cm foam-embedded coil from Example 2 was cut into about 4-mm segments. Coil segments were then placed into Siliconized Eppendorf tubes. The coil segments were wet with 0.5 milliliters of 70% ethanol, and then washed twice with 1 milliliter of phosphate buffered saline (PBS). The coil segments were incubated with 100 microliters of fibronectin probe solution. The solution was purchased from Sigma Chemical Co. (St. Louis, Mo.). and was radiolabeled by iodine 125 at Lofstrand Labs Limited (Gaithersburg, Md.). The incubation was for 1 hour at 37° C. Afterwards, the incubated coil segments were washed three times with 1 milliliter 0.1% Triton in PBS. The coil segments were transferred to a scintillation vial, and the radioactivity of the samples was counted. Absorption of fibronectin on foamed coils of Example 2 was about three fold higher than on the bare coils under similar treatment.

As can be appreciated, numerous variations of the present invention exist to treat the limitless variations in blood vessel and vascular malformation anatomy. It is within the scope of the present invention to use various known, detachable positioning mechanisms to deploy the vascular embolization device of the present invention.

That which is claimed is:

1. A vascular embolization device adapted for delivery to a position within a patient's blood vessel comprising an elongated coil having a lumen, said coil and lumen prior to said delivery being at least partially embedded in an elongated foam member comprising a flexible, biodegradable, open and interconnecting cell foam material having embolic characteristics, and capable of allowing cell proliferation into the open cell foam interior, the foam member having an average pore size of 5-100 microns, said elongated foam member having an outer diameter which, in uncompressed condition, is no more than 0.006 inch greater than the outer diameter of the elongated coil.

2. The device of claim 1 in which the uncompressed, outer diameter of the elongated foam member is no more than about 0.004 inch greater than the outer diameter of the elongated coil.

3. The device of claim 1 in which the uncompressed, outer diameter of said foam member is no more than about 0.016 inch, and the outer coil diameter is about 0.01-0.014 inch.

4. The device of claim 1 in which the lumen of the coil is filled with said foam member.

5. The device of claim 1 in which the foam member comprises a polymer formulation that is flexible and cohesive, with or without the presence of water.

6. The device of claim 1 in which the foam member is elastomeric.

7. The device of claim 1 in which substantially the entire length of said elongated coil is embedded in the elongated foam member.

8. The device of claim 1 in which the foam member comprises a PCL/PGA copolymer.

9. The device of claim 8 in which the lumen of the coil is filled with said foam member.

\* \* \* \* \*